United States Patent [19]

Honkanen et al.

[11] Patent Number: 4,655,752
[45] Date of Patent: Apr. 7, 1987

[54] SURGICAL CANNULA

[75] Inventors: George P. Honkanen, N. Scituate; John C. Strahan, Arlington; Philip R. Lichtman, Newton, all of Mass.

[73] Assignee: Acufex Microsurgical, Inc., Norwood, Mass.

[21] Appl. No.: 849,173

[22] Filed: Apr. 7, 1986

Related U.S. Application Data

[63] Continuation of Ser. No. 544,552, Oct. 24, 1983, abandoned.

[51] Int. Cl.$^4$ .............................................. A61M 5/00
[52] U.S. Cl. ...................................... 604/256; 604/167
[58] Field of Search ....................... 604/167, 169, 256; 251/149.1; 137/230, 846, 849

[56] References Cited

U.S. PATENT DOCUMENTS

| | | | |
|---|---|---|---|
| 4,000,739 | 1/1977 | Stevens | 604/167 X |
| 4,424,833 | 1/1984 | Spector et al. | 137/849 |
| 4,436,519 | 3/1984 | O'Neill | 604/256 |
| 4,438,801 | 1/1981 | Timmermans | 604/256 |

Primary Examiner—Dalton L. Truluck
Attorney, Agent, or Firm—Schiller, Pandiscio & Kusmer

[57] ABSTRACT

A surgical cannula having a first seal member having a substantially conical shape and an opening at the tip thereof, and a second seal member having a substantially conical shape and a slit at the tip thereof, whereby (a) when an instrument is inserted into the cannula, the instrument can pass through the first and second seal members into proximity with a surgical site located beneath the cannula, and fluid entering the cannula from the site will force the first seal member to close around the instrument and form a tight seal therewith so as to prohibit fluid from passing out of the cannula and (b) when no instrument is inserted into the cannula, fluid entering the cannula from the site will force the conical second seal member to close tightly on its slit and thereby form a tight seal so as to prohibit fluid from passing out of the cannula.

11 Claims, 6 Drawing Figures

U.S. Patent   Apr. 7, 1987   4,655,752
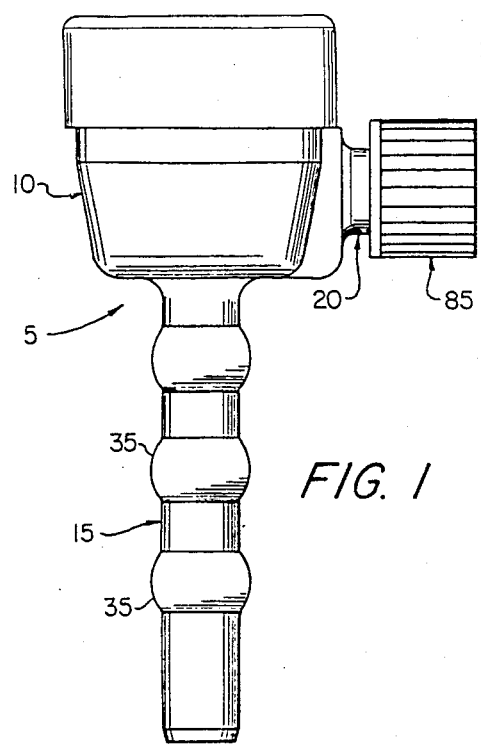
FIG. 1
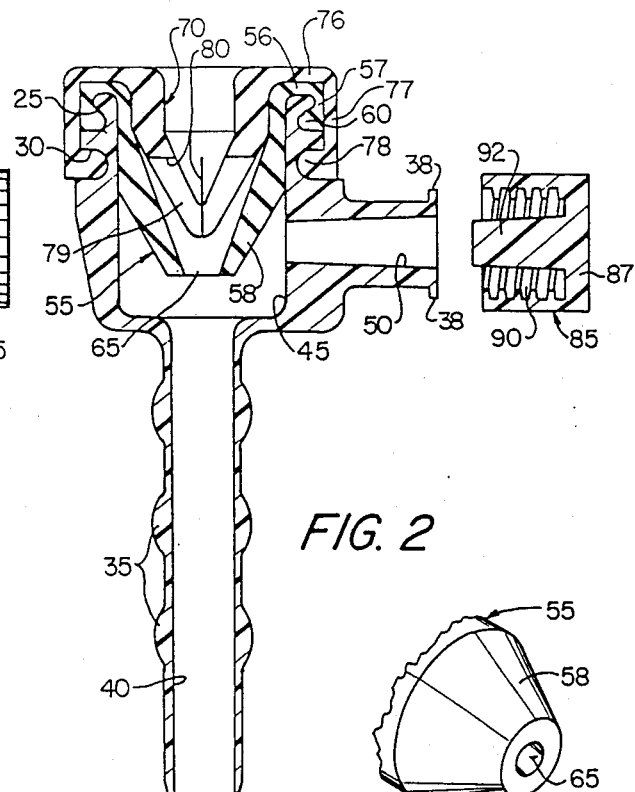
FIG. 2
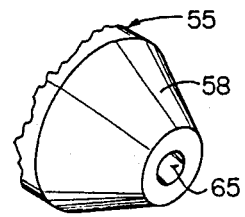
FIG. 4
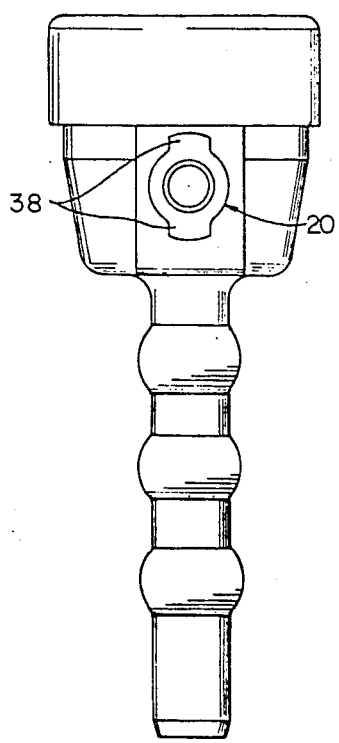
FIG. 3
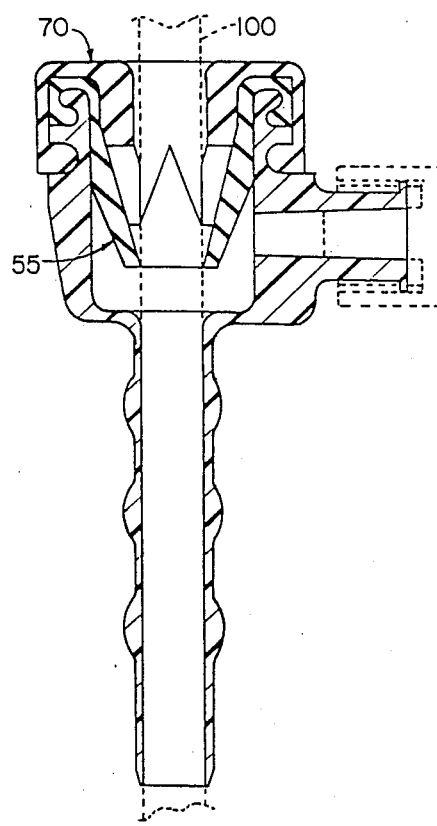
FIG. 6
FIG. 5

SURGICAL CANNULA

This application is a continuation of Ser. No. 544,552, filed Oct. 24, 1983, now abandoned.

FIELD OF THE INVENTION

This invention relates to surgical instruments in general, and more particularly to surgical cannulae.

BACKGROUND OF THE INVENTION

Surgical cannulae are well known in the art. Such instruments are essentially tube-like elements which are inserted into surgical openings so that they line and maintain the openings. Surgical cannulae can be used for a wide variety of different purposes, and their particular construction tends to vary accordingly.

For example, some surgical cannulae are designed to serve as an irrigation passageway between the surgical site and the region outside the body. In this case, the cannulae, sometimes referred to as "irrigation cannulae", tend to be of relatively simple construction, and are frequently little more than a hollow tube, with or without an associated stopcock.

Other surgical cannulae are designed to serve as a protective liner for the surgical opening. These cannulae, sometimes referred to as "instrument cannulae", are used to minimize tissue trauma during the insertion, use and removal of surgical instruments to and from the surgical site. Since the surgical site is frequently well irrigated, particularly during arthroscopic surgery, these cannulae typically have some sort of fluid seal disposed across the cannula's central opening so as to prevent the disruptive backflow of fluid through the cannula.

Ideally, the fluid seal in an instrument cannula should be able to do three things well: first, it should be able to pass an instrument easily therethrough so that the instrument can reach the surgical site from a point outside the body; second, it should be able to establish an effective fluid seal about an instrument inserted into the cannula, and maintain it while the instrument is worked around the surgical site, so as to prevent the annoying backflow of fluid through the cannula; and third, it should be able to establish an effective fluid seal on its own across the cannula's central opening when no instrument is inserted into the cannula.

Unfortunately, fluid seals of the sort currently found in instrument cannulae have proven incapable of satisfying all three of these requirements. For example, at least one existing instrument cannula uses as its fluid seal a single flat resilient member which extends across the cannula's central opening. The flat resilient member has a slit at its center which permits an instrument to pass through the member to reach the surgical area. Unfortunately, however, this seal arrangement tends to leak badly, both when there is an instrument inserted in the cannula and when there is not.

An alternative seal arrangement is used in at least one other existing instrument cannula. This alternative seal arrangement comprises three flat parallel resilient members disposed across the cannula's central opening. Each resilient member has a single linear slit disposed therein which extends in a radial direction through the member's center point so as to allow an instrument access to the surgical site. These slits are oriented so that they extend at oblique angles relative to one another, in order to minimize the disruptive backflow of fluid through the cannula. While such a seal arrangement is somewhat better at eliminating fluid backflow than the aforementioned single flat seal arrangement, it still allows significant leakage to occur both when an instrument is inserted in the cannula and when one is not.

OBJECTS OF THE INVENTION

Accordingly, one of the objects of the present invention is to provide an instrument cannula which has an improved fluid seal arrangement therein, whereby the cannula can effectively seal against annoying fluid backflow both when an instrument is inserted in the cannula and when one is not.

Another object of the invention is to provide an instrument cannula which can alternately serve as an irrigation cannula, so that less cannulae need be emplaced during a given surgical procedure, and so that the surgery can be conducted more quickly and with less tissue trauma.

Still another object is to provide an instrument cannula which can alternately serve as a companion sheath for an endoscope, so that less cannulae and endoscopic sheaths need be emplaced during a given surgical procedure, and so that surgery can be conducted more quickly and with less tissue trauma.

Yet another object is to provide a surgical cannula which utilizes an improved exterior shape so as to enhance the ability of the cannula to remain in place and make a tight seal with the surrounding tissue, without causing excess trauma to the tissue.

SUMMARY OF THE INVENTION

These and other objects are achieved by the present invention, which comprises a surgical cannula having, in its preferred embodiment, a housing, a first seal member, and a second seal member, with the housing having a top end and a bottom end, a central opening extending through the housing from said top end to said bottom end, and a side opening intercepting the central opening and fitted with a removable cap. The first seal member has a substantially conical shape and a circular opening at the tip thereof, and the second seal member has a substantially conical shape and a cruciform slit at the tip thereof. Additionally, the first and second seal members are disposed in the housing's central opening substantially above the side opening, with the tips of the seal members directed towards the bottom end of the housing, whereby (a) when an instrument is inserted in the cannula, the instrument can pass easily through the circular opening in the first seal member and the cruciform slit in the second seal member so as to reach the surgical site disposed beneath the cannula's bottom end, and fluid entering the housing's central opening via said bottom end will force the conical first seal member to close around the instrument and thereby form a tight seal therewith so that no fluid can flow out the top end of the cannula housing, (b) when no instrument is inserted in the cannula, fluid entering the housing's central opening from the bottom end of the housing will force the conical second seal member to close tightly on its cruciform slit and thereby form a tight seal so that no fluid can flow out the top end of the cannula housing, and (c) when no instrument closes off the bottom end of the central opening, fluid entering the housing's central opening from the bottom end of the housing can flow out the side opening if that opening's removable cap is removed.

BRIEF DESCRIPTION OF THE DRAWINGS

Still other objects and features of the present invention will be more fully disclosed or rendered obvious in the following detailed description of the preferred embodiment of the invention, which is to be considered together with the accompanying drawings wherein like numbers refer to like parts, and further wherein:

FIG. 1 is an elevational view showing the left side of a cannula which comprises the preferred form of the invention;

FIG. 2 is an exploded longitudinal sectional view of the said cannula;

FIG. 3 is an elevational view showing the rear side of the cannula, but with the cannula's stopcock cap removed;

FIG. 4 is a fragmentary perspective view of the tip portion of the cannula's first seal member;

FIG. 5 is a fragmentary perspective view of the tip portion of the cannula's second seal member; and FIG. 6 is a fragmentary elevational view partially in section showing the cannula and an associated surgical instrument acting in cooperation with one another.

DETAILED DESCRIPTION OF THE PREFERRED EMBODIMENT

Looking first at FIGS. 1–3, the preferred form of surgical cannula comprises a housing 5 which has an expanded upper section 10, a reduced lower section 15, and a side extension 20. Upper section 10, lower section 15 and side extension 20 are all formed integral with one another, preferably from a selected rigid or semi-rigid plastic. The housing's upper section 10 has a pair of parallel, circumferentially-extending grooves 25 and 30 in its outer surface. The housing's lower section 15 has a plurality of circumferential ribs or ridges 35 spaced along its outer surface. The housing's side extension 20 has a pair of flanges 38 disposed in diametrically-opposed relation at the end of the extension. Each flange has a circularly-curved outer surface. A central bore 40 in the housing's lower section 15 intersects a counterbore 45 in the housing's upper section 10. Another axial bore 50 in side extension 20 intersects counterbore 45 intermediate its length. Bore 50 is preferably tapered as shown.

Looking next at FIGS. 2 and 4, the surgical cannula also comprises two seal members 55 and 70. Seal member 55 is formed from a soft elastomeric material, e.g., a silicone rubber, and has a generally conically shaped portion 58 at one end. The other end of seal member 55 has a peripheral flange 56 with a lip 57 having an inwardly facing rib 60. Conical portion 58 of seal member 55 has a circular opening 65 at its tip. Seal member 55 is mounted to housing 5 so that its lip 57 surrounds the housing and its rib 60 resides in groove 25 and bears against the housing's exterior surface, whereby the seal's conical portion 58 extends down into counterbore 45 and its circular opening 65 is substantially aligned with bore 40.

Looking next at FIGS. 2 and 5, the second seal member 70 is substantially cup shaped and also is formed from a soft elastomeric material, e.g., a silicone rubber. One end of seal 70 is open and has a peripheral flange 76 with a lip 77 having an inwardly facing rib 78. The opposite or tip end of seal member 70 is closed but is cut by one or more slits 80 into two or more flexible lip sections 79. Preferably it is cut by a diametrical pair of slits 80 displaced 90 from one another so as to form a cruciform cut pattern defining four like lip portions 79. Seal member 70 is mounted to housing 5 so that its rib 78 rests in and bears against the housing's exterior groove 30. The body of seal member 70 extends down into counterbore 45 substantially coaxial with and above the body of first seal member 55, with the cruciform cut pattern of slits 80 being substantially aligned with circular opening 65 of seal member 55. The flange 76 and lip 77 of seal member 70 engage and grip the flange 56 and lip 57 of seal member 55.

Looking next at FIGS. 1–3, the surgical cannula also comprises a stopcock cap 85. Cap 85 has a screw threaded blind hole 90 on one end which cooperates with the aforementioned flanges 38 on rear extension 20 so as to form a screw-on cap arrangement. Cap 85 also has a tapered central post 92 extending lengthwise of blind hole 90 which serves to securely plug bore 50 against fluid flow when the end wall 87 of cap 85 is seated against rear extension 20. As a consequence of the foregoing construction, rear extension 20 and cap 85 together form a stopcock mechanism.

The surgical cannula 5 is utilized as follows. First, it is emplaced in a surgical opening in the body of a human or animal patient so that the housing's lower section 15 resides inside the body and the housing's upper section 10 resides outside the body. When so emplaced, the circumferential ridges 35 of lower section 15 bear against the surrounding tissue in a non-traumatic manner so as to hold the cannula securely in place and make a good seal between the cannula and the surrounding tissue. Access may then be had to the surgical site through the cannula, either via counterbore 45, cruciform slit 80 of seal member 70, circular opening 65 of seal member 55, and bore 40, or alternatively through bore 50, counterbore 45, and bore 40.

More particularly, if it should be desired to utilize the cannula as an instrument cannula, a surgical instrument of selected diameter is inserted through the cannula to the surgical site via counterbore 45, cruciform slit 80 of seal member 70, circular opening 65 of seal member 55, and bore 40. The diameter of the surgical instrument is coordinated with the size of the circular opening 65 so that the elastomeric seal member 55 can form an effective fluid seal about the instrument and maintain it while the instrument is worked around the surgical site. More particularly, circular opening 65 of elastomeric seal member 55 is sized so that it is slightly smaller in its unstressed state than the diameter of an instrument being passed through the seal member, whereby the seal member will make a snug fit about the instrument and thereby prevent fluid from passing between it and the instrument and escaping out the top end of the cannula. In this context it should be noted that the substantially conical shape of seal member 55 assists in the formation of a tight seal about the instrument, since fluid pressure will tend to cause the conical seal member to "collapse" inward onto the instrument and make it adhere more securely thereto.

FIG. 6 illustrates in detail how an instrument 100 interacts with the cannula and its two seal members when it is inserted in the cannula. In this respect it is to be appreciated that instrument 100 can be a conventional surgical instrument such as a cannula knife, or it can be an endoscope of the sort well known in the art, in which case the cannula will essentially function as the endoscope's companion sheath.

In order to facilitate the passage of surgical instruments through seal members 55 and 70, it is preferred that the seal members be coated with a lubricant, e.g., a silicone compound. This arrangement helps to assure that the circular opening 65 of seal member 55 can be sized sufficiently small to form an effective seal about an instrument, without hampering instrument access to the surgical site.

When the surgical instrument is subsequently withdrawn from the cannula, seal member 70 will act to prevent fluid from escaping out the top of the cannula. More particularly, as fluid tries to escape out the top end of the cannula, its pressure will force the bottom end of seal member 70 to contract at its cruciform slit 80, causing the lips 79 to move tightly into engagement with one another so as to render the bottom end of the seal 70 substantially impervious to fluid flow. In other words, when the inserted instrument is removed from the cannula, seal member 70 will provide a substantially fluid-tight seal across the central opening of the cannula so that no fluid can escape out the top end of the cannula.

If it is alternatively desired to use the cannula as an irrigation device, all that needs be done is to remove stopcock cap 85 from side extension 20. Such removal of the rear cap allows access to the surgical site via bore 50, counterbore 45 and bore 40, whereby fluid may be introduced to or removed from the surgical site. It will of course be appreciated that the cannula can serve simultaneously as both an instrument cannula and an irrigation cannula, so long as the instrument being used with the cannula is not so large as to close off bore 40 to fluid flow, i.e., so that fluid may flow through bore 40 in the space left between the instrument and the walls of the bore.

Modifications Of The Preferred Embodiment

It is, of course, possible to modify the foregoing preferred embodiment of the invention without departing from the scope of the present invention.

Thus, for example, the cannula's housing may be formed with more or less than the one stopcock mechanism shown.

Another possible modification is to provide the cannula's stopcock with a simple check valve of the sort well known in the art to assure fluid flow in only one direction through the stopcock, e.g., a check valve allowing fluid to be injected into side extension 20 from an external source but preventing fluid from leaving the cannula via side extension 20.

Another obvious change is to line bore 40 with a metallic liner near the bottom end of the cannula for use as a drilling guide.

It is also contemplated that seal member 55 may be formed with a cruciform slit at its tip instead of a circular opening, and at the same time seal member 70 would have a circular opening at its top instead of a cruciform slit.

Furthermore, one might form second seal 70 with a single diametrically-extending slit 80 at its tip instead of the cruciform slit described and illustrated previously.

Other changes of similar type and purpose will be obvious to a person skilled in the art and well within the scope of the present invention.

Advantages Of The Invention

Numerous advantages are obtained by using a cannula made according to the present invention instead of a conventional surgical cannula.

First, the present invention provides improved fluid seals that can effectively seal against troublesome fluid backflow both when an instrument is inserted in the cannula and when one is not.

Second, the present invention comprises a cannula which can alternately serve as an instrument or irrigation cannula, so that less cannulae need be emplaced during a given surgical procedure and so that the surgery can be conducted more quickly and with less tissue trauma.

Third, the present invention comprises an instrument cannula which can alternately serve as a companion sheath for an endoscope, thereby reducing the number of such devices which need be emplaced during a given surgical procedure and enabling surgery to be conducted more quickly and with less tissue trauma.

Fourth, the present invention has an improved exterior shape which enhances the ability of the cannula to remain in place and make a tight seal with the surrounding tissues, without any attendant increase in trauma to the tissue.

What is claimed is:

1. A surgical cannula comprising:
   a hollow housing;
   a first seal member; and
   a second seal member;
   said housing having a top end, a bottom end, and a side wall defining an interior passageway extending from said top end to said bottom end;
   said first seal member being hollow and conically tapered and having a top end with a relatively large top end opening and a bottom end with a relatively small bottom end opening, said first seal member being formed from a soft elastomeric material and being disposed in said interior passageway so that its bottom end is directed towards said bottom end of said housing, with said bottom end of said first seal member being disposed within and spaced from said side wall;
   said second seal member being cup shaped and having an open top end and a conically tapered bottom end, said second seal member being formed from a soft elastomeric material and being disposed in said interior passageway so taht its bottom end is directed towards said bottom end of said housing, with said bottom end of said second seal member being disposed within and spaced from said side wall so as to define a continuous annular gap therebetween, and said second seal member having at least one slit in said bottom end which allows said seal member to expand radially at said bottom end into said annular gap and towards said side walls so as to form a variable size opening at said slit;
   whereby (a) when an instrument is inserted into said housing via said top end, said instrument can pass through said first and second seal members into proximity with a surgical site beneath said bottom end of said housing, and fluid entering said interior passageway via said bottom end of said housing will force said first seal member to close around said instrument and form a tight seal therewith so that no fluid can flow out said top end of said housing, and (b) when no instrument is inserted into said housing, fluid entering said interior opening via said bottom end of said housing will force the bottom end of said second seal to contract in the region of said at least one slit and thereby form a tight seal so that no fluid can exit said housing via said top end thereof.

2. A surgical cannula according to claim 1 wherein said housing has a side opening intercepting said interior passageway, whereby fluid entering said interior passageway via said bottom end of said housing can be discharged from said housing by flowing out said side opening.

3. A surgical cannula according to claim 2 further including removable closure means for closing off said side opening.

4. A surgical cannula according to claim 1 wherein one of said seal members is disposed substantially within the other one of said seal members.

5. A surgical cannula according to claim 1 wherein said first seal member overlaps said top end of said housing.

6. A surgical cannula according to claim 5 wherein said second seal member overlaps said first seal member at said top end of said housing.

7. A surgical cannula according to claim 6 wherein said tapered bottom end of said second seal member is disposed substantially within said hollow first seal member.

8. A surgical cannula according to claim 1 wherein said second seal member has two slits intersecting one another in a cruciform pattern.

9. A surgical cannula according to claim 1 wherein said at least one slit constitutes a linear, i.e., straight, cut.

10. A surgical cannula according to claim 1 wherein said housing comprises an outer surface and first and second circumferentially extending grooves formed in said outer surface adjacent said top end of said housing, said first groove residing closer to said top end of said housing than said second groove, and further wherein said first seal extends around said top end of said housing and comprises an inwardly facing circumferentially extending rib disposed in said first groove and said second seal extends around said top end of said housing and comprises an inwardly facing circumferentially extending rib disposed in said second groove.

11. A surgical cannula comprising:

a hollow housing, said hollow housing comprising a top end, a bottom end, and an interior passageway extending from said top end to said bottom end;

a first seal member, said first seal member being hollow and conically tapered and having a top end with a relatively large top end opening and a bottom end with a relatively small bottom end opening, said first seal member being formed from a soft elastomeric material and being disposed within said interior passageway so that its bottom end is directed towards said bottom end of said housing, with said bottom end of said first seal member being disposed within and spaced from said housing; and a second seal member, said second seal member being cup shaped and having an open top end and a conically tapered bottom end, said second seal member being formed from a soft elastomeric material and being disposed within said interior passageway so that its tapered bottom end is directed towards said bottom end of said housing, with said bottom end of said second seal member being disposed within and spaced from said hollow first seal member so as to define a continuous annular gap therebetween, and said second seal member having at least one slit in said bottom end which allows said seal member to expand radially at said bottom end into sad annular gap and towards said surrounding first seal member so as to form a variable size opening;

whereby (a) when an instrument is inserted into said housing via said top end, said instrument can pass through said first and second seal members into proximity with a surgical site beneath said bottom end of said housing, and fluid entering said interior passageway via said bottom end of said housing will force said first seal member to close around said instrument and form a tight seal therewith so that no fluid can flow out said top end of said housing, and (b) when no instrument is inserted into said housing, fluid entering said interior opening via said bottom end of said housing will force the bottom end of said second seal to contract in the region of said at least one slit and thereby form a tight seal so that no fluid can exit said housing via said top end thereof.

* * * * *

UNITED STATES PATENT AND TRADEMARK OFFICE
CERTIFICATE OF CORRECTION

PATENT NO. : 4,655,752

DATED : April 7, 1987

INVENTOR(S) : George P. Honkanen et al.

It is certified that error appears in the above-identified patent and that said Letters Patent is hereby corrected as shown below:

Claim 1, column 6, line 45, "taht" should be -- that --.

Claim 1, column 6, line 53, "walls" should be -- wall --.

Signed and Sealed this

Eighth Day of September, 1987

Attest:

DONALD J. QUIGG

*Attesting Officer*      *Commissioner of Patents and Trademarks*